United States Patent
Clouatre et al.

(10) Patent No.: US 11,219,610 B2
(45) Date of Patent: *Jan. 11, 2022

(54) BOLUS DOSE OF HYDROXYCITRIC ACID WITH GLYCEROL

(71) Applicant: GLYKON TECHNOLOGIES GROUP, LLC, Seattle, WA (US)

(72) Inventors: Dallas L. Clouatre, Seattle, WA (US); Daniel E. Clouatre, Seattle, WA (US); Brad J. Douglass, Seattle, WA (US)

(73) Assignee: GLYKON TECHNOLOGIES GROUP, LLC, Seattle, WA (US)

( * ) Notice: Subject to any disclaimer, the term of this patent is extended or adjusted under 35 U.S.C. 154(b) by 176 days.

This patent is subject to a terminal disclaimer.

(21) Appl. No.: 16/815,688

(22) Filed: Mar. 11, 2020

(65) Prior Publication Data

US 2020/0206171 A1 Jul. 2, 2020

Related U.S. Application Data

(63) Continuation of application No. 16/452,239, filed on Jun. 25, 2019, now Pat. No. 10,624,868, which is a continuation of application No. 15/975,424, filed on May 9, 2018, now Pat. No. 10,376,483, which is a continuation of application No. 15/701,107, filed on Sep. 11, 2017, now Pat. No. 9,993,448, which is a continuation of application No. 14/614,201, filed on Feb. 4, 2015, now Pat. No. 9,789,076.

(60) Provisional application No. 62/081,161, filed on Nov. 18, 2014.

(51) Int. Cl.

| | | |
|---|---|---|
| *A61K 36/00* | (2006.01) | |
| *A61K 31/194* | (2006.01) | |
| *A61K 47/10* | (2017.01) | |
| *A61K 45/06* | (2006.01) | |
| *A61K 36/74* | (2006.01) | |
| *A61K 31/216* | (2006.01) | |
| *A61K 36/42* | (2006.01) | |
| *A61K 36/185* | (2006.01) | |
| *A61K 9/14* | (2006.01) | |
| *A61J 1/14* | (2006.01) | |
| *A61K 31/00* | (2006.01) | |
| *A61K 9/00* | (2006.01) | |
| *A61K 31/047* | (2006.01) | |

(52) U.S. Cl.
CPC .......... *A61K 31/194* (2013.01); *A61J 1/1412* (2013.01); *A61K 9/0053* (2013.01); *A61K 9/0095* (2013.01); *A61K 9/14* (2013.01); *A61K 9/145* (2013.01); *A61K 31/00* (2013.01); *A61K 31/047* (2013.01); *A61K 31/216* (2013.01); *A61K 36/185* (2013.01); *A61K 36/42* (2013.01); *A61K 36/74* (2013.01); *A61K 45/06* (2013.01); *A61K 47/10* (2013.01)

(58) Field of Classification Search
None
See application file for complete search history.

(56) References Cited

U.S. PATENT DOCUMENTS

| | | | |
|---|---|---|---|
| 3,764,692 A | 10/1973 | Lowenstein | |
| 5,626,849 A | 5/1997 | Hastings et al. | |
| 5,783,603 A | 7/1998 | Majeed et al. | |
| 6,476,071 B1 | 11/2002 | Clouatre et al. | |
| 8,367,864 B2 | 2/2013 | Moffett et al. | |
| 2006/0141030 A1 | 6/2006 | Clouatre | |

FOREIGN PATENT DOCUMENTS

WO    WO 2008/140444    11/2008

OTHER PUBLICATIONS

Heymsfield, et al., "Garcinia cambogia (Hydroxycitric Acid) as a Potential Antiobesity Agent", JAMA, (Nov. 11, 1998), vol. 280, No. 18.

Onakpoya, et al., "The Use of Garcinia Extract (Hydroxycitric Acid) as a Weight loss Supplement: A Systematic Review and Meta-Analysis of Randomised Clinical Trials", Journal of Obesity (Oct. 2010).

Saini, et al., "Effect of Medication Dosing Frequency on Adherence in Chronic Diseases", The American Journal of Managed Care (Jun. 2009).

Sullivan, et al., "Metabolic regulation as a control for lipid disorders. I. Influence of (--------)-hydroxycitrate on experimentally induced obesity in the rodent", The American Journal of Clinical Nutrition (May 1977), pp. 767-776.

*Primary Examiner* — Michael V Meller
(74) *Attorney, Agent, or Firm* — Karl Bozicevic; Bozicevic, Field & Francis LLP

(57) ABSTRACT

A method of delivering a daily dose of hydroxycitric acid in the form of a salt as a single bolus that is as effective or more so than the same amount of active delivered via two or three administrations (b.i.d. or t.i.d.) using current delivery modalities. The method reduces the rate of occurrence of common adverse events with hydroxycitric acid salts, and reduces the occurrence of reverse effects on diets high in fat and/or alcohol. The method improves the uptake of the active compound thereby reducing the dose required.

5 Claims, No Drawings

BOLUS DOSE OF HYDROXYCITRIC ACID WITH GLYCEROL

FIELD OF THE INVENTION

The invention is related to the field of drug dosages and delivery and particularly to a combination of (−)-hydroxycitric acid salts with glycerol as a single bolus dose.

BACKGROUND OF THE INVENTION (−)-Hydroxycitric acid (abbreviated herein as HCA) is a naturally-occurring substance found chiefly in fruits of the species of *Garcinia*. HCA has been the subject of extensive investigations, yet in many areas has remained more "promising" than effective due to numerous issues regarding stability, bioavailability, the requirement for elevated dosages and the need for two or more dosing per day to avoid the even larger requirements for efficacy if ingested only as a bolus dose. Although HCA and several synthetic derivatives of citric acid have been investigated in regard to their ability to inhibit the production of fatty acids from carbohydrates, to suppress appetite, and to inhibit weight gain (Sullivan A C, Triscari J. Metabolic regulation as a control for lipid disorders. I. Influence of (−)-hydroxycitrrate on experimentally induced obesity in the rodent. American Journal of Clinical Nutrition 1977; 30:767), the record is, at best, uneven with regard to efficacy in these and other areas.

Weight loss benefits were first ascribed to HCA, its salts and its lactone in U.S. Pat. No. 3,764,692 granted to John M. Lowenstein in 1973. The claimed mechanisms of action for HCA, most of which were originally put forth by researchers at the pharmaceutical firm of Hoffmann-La Roche, have been summarized in at least two United States Patents. In U.S. Pat. No. 5,626,849 these mechanisms are given as follows: "(−) HCA reduces the conversion of carbohydrate calories into fats. It does this by inhibiting the actions of ATP-citrate lyase, the enzyme that converts citrate into fatty acids and cholesterol in the primary pathway of fat synthesis in the body. The actions of (−) HCA increase the production and storage of glycogen (which is found in the liver, small intestine and muscles of mammals) while reducing both appetite and weight gain. (−) Hydroxycitric acid also causes calories to be burned in an energy cycle similar to thermogenesis . . . (−) HCA also increases the clearance of LDL cholesterol . . . ." U.S. Pat. No. 5,783,603 further argues that HCA serves to disinhibit the metabolic breakdown and oxidation of stored fat for fuel via its effects upon the compound malonyl CoA.

Literature on this compound has been reviewed by a number of authors, and new mechanisms of action and other findings continue to be published regularly. Technical and other data published over a period of more than five decades continues to support unequivocally the early findings by Roche researchers in the 1970s that the efficacy of a bolus dose is far below that of a much smaller amount of the compound given via two or more doses per day. Using an animal model measuring total weight gain and food consumption in rats administered trisodium hydroxycitrate orally for 30 days, it was established that the lowest effect dosage was 0.33 mmoles/kg body weight given twice daily for a total of 0.66 mmoles/kg leading to 62 percent of the weight gain of controls and to 87 percent of the food consumption of controls. It took 2.63 mmoles/kg to achieve this same degree reduction in weight gain (64 percent) and food consumption (83 percent). Lesser amounts given by bolus did not lead to significant reductions in weight gain in this model. (Sullivan, A. C., J. Triscari, J. G. Hamilton, O. N. Miller, and V. R. Wheatley. 1974. Effect of (−)-hydroxycitrate upon the accumulation of lipid in the rat: I. Lipogenesis. Lipids 9:121-128.)

The Roche animal dosages should be put in perspective as the likely lowest efficacious human dose under similar conditions of less than 10% calories from fat in the diet. At 0.33 mmol HCA b.i.d., the human dosage is 208 mg×0.33× 70 kg=4.8 grams of HCA per dose×2=9.6 grams HCA/ day=16 grams of a 60% salt. Using the normal rat-to-human multiplier for calculating the small animal effect (Freireich E J, Gehan E A, Rall D P, Schmidt L H, Skipper H E. Quantitative comparison of toxicity of anticancer agents in mouse, rat, hamster, dog, monkey, and man. Cancer Chemother Rep. 1966 May; 50(4):219-44), an appropriate dose for humans would be closer to 9.6÷5=1.92 grams hydroxycitric acid content b.i.d. on an extremely low fat diet and assuming the material is supplied via a salt that is equivalent to pure trisodium hydroxycitrate in efficacy and is delivered without food effect on uptake, which has been shown to reduce the bioavailability of the potassium-calcium salt in humans to approximately 8 percent (Loe YCl, Bergeron N, Rodriguez N, Schwarz J M. Gas chromatography/mass spectrometry method to quantify blood hydroxycitrate concentration. Anal Biochem. 2001 May 1; 292(1):148-54). Inasmuch as humans seldom eat 10 percent fat diets except under conditions of food scarcity or medical restriction, the minimal dose for efficacy generally is higher, as indicated by the successes and failures of human trials.

Clinical trials examining HCA and weight loss have used dosages ranging from 1 gram to 2.8 grams HCA per day via two or three intakes. The 2.8 gram dosage more closely matches the animal-to-human extrapolation above and is the amount that has given the most consistently positive result in trials. (Onakpoya I, Hung S K, Perry R, Wider B, Ernst E. The Use of *Garcinia* Extract (Hydroxycitric Acid) as a Weight loss Supplement: A Systematic Review and Meta-Analysis of Randomised [sic] Clinical Trials. J Obes. 2011; 2011:509038.) Calcium-only HCA salts have not proven effective and comparative animal trials have demonstrated that potassium- and potassium-magnesium HCA salts are more active than potassium-calcium salts. (Louter-van de Haar J, Wielinga P Y, Scheurink A J, Nieuwenhuizen A G. Comparison of the effects of three different (−)-hydroxycitric acid preparations on food intake in rats. Nutr Metab (Lond). 2005 Sep. 13; 2:23.) (Clouatre D, Preuss H G. Potassium Magnesium Hydroxy-citrate at Physiologic Levels Influences Various Metabolic Parameters and Inflammation in Rats. Current Topics in Nu-traceutical Research 2008; 6: 201-210.) The initial studies of HCA all used a virtually pure trisodium salt. However, recent studies often have failed to indicate the form of HCA used. It should be noted in passing that neither the free acid form nor the lactone of HCA is suitable for chronic use for a number of reasons, e.g., the chelation of transition metals (such as zinc) from the body, throat irritation and other similar issues revealed in the literature on HCA.

Notably, few current authors address a major issue with HCA supplementation, to wit, that there can be a reverse effect, i.e., weight gain, on diets containing significant amounts of alcohol or fat. As discovered decades ago, "no hydroxycitrate inhibition of acetate or ethanol incorporation [into fatty acid synthesis] was observed" in experiments designed to examine this issue. (Brunengraber H, Lowenstein J M. Effect of (−)-hydroxycitrate on ethanol metabolism. FEBS Lett. 1973 Oct. 15; 36(2):130-2.) Very low calorie diets necessarily cause the body to rely upon fat stores for fuel. Although HCA has been shown to shift the body towards preferential metabolism of fat for fuel, there is a point at which dietary reliance on fats or alcohol, whether through food choices or dieting, negates the impact of HCA. This was demonstrated in Roche's pair feeding study in which animals artificially restricted in diet to the same number of calories as induced by HCA feeding actually lost slightly more weight than the HCA arms. (Sullivan, A. C., J. Triscari, J. G. Hamilton, O. N. Miller, and V. R. Wheatley. 1974. Effect of (−)-hydroxycitrate upon the accumulation of lipid in the rat: I. Lipogenesis. Lipids 9:121-128.) Similarly, in a large clinical trial in which both the active and the control arms were placed on high fiber, low calorie diets, both arms lost weight, but the control arm lost more. (Heymsfield S Bl, Allison D B, Vasselli J R, Pietrobelli A, Greenfield D, Nunez C. *Garcinia cambogia* (hydroxycitric acid) as a potential antiobesity agent: a randomized controlled trial. JAMA. 1998 Nov. 11; 280(18):1596-600.) The tendency towards a reverse effect on high fat and/or high alcohol diets is a result of these diets making acetyl units available from beta-oxidation rather than from the export of citrate from the Citric Acid Cycle, which is the more common path under normal metabolism. Increasing the amount of HCA ingested and/or, and more successfully, using more active forms of HCA, reduces or eliminates the likelihood of a reverse effect under most conditions. This point is demonstrated in our U.S. Pat. No. 6,476,071, which shows that on a 30 percent fat diet and in line with the findings of Louter-van de Haar et al. cited above, a relatively pure potassium HCA salt led to a significant reduction in weight gain whereas the potassium-calcium HCA salt led to significant increase in weight gain relative to control. In other words, the potassium-calcium HCA salt suffered a reverse effect on a 30 percent fat diet, which for rodents is a high fat diet.

Dose compliance is yet another challenge. It is well established that compliance declines significantly as the required dose moves from once per day to multiple doses per day. The vast preponderance of studies have found that individuals are more compliant with once-daily compared with twice-daily or thrice-daily treatment regimens. (Saini S Dl, Schoenfeld P, Kaulback K, Dubinsky M C. Effect of medication dosing frequency on adherence in chronic diseases. Am J Manag Care. 2009 Jun. 1; 15(6):e22-33.) One study states directly, mentioning most of the important parameters for consideration, "Reducing the number of daily doses through extended-release formulations or newer drugs has frequently been shown to provide the patient with better symptom control in a number of disease states. Overall improvements were seen in adherence, patient quality of life, patient satisfaction, and costs. However, results of some studies indicate that not all patients, medications, or diseases may be candidates for reduced dosing due to the potential effects on symptom control, incidence of adverse events, and overcompensation for missed doses." (Richter Al, Anton S E, Koch P, Dennett S L. The impact of reducing dose frequency on health outcomes. Clin Ther. 2003 August; 25(8):2307-35.)

The instant invention addresses the concerns raised above, which point to a significant need for an approach to HCA supplementation to reduce the number of daily doses to one bolus dose without an increase in the total dosage or adverse events, to improve uptake so that lower dosages can be employed, to lessen the time window required for uptake such that the known food effect found with HCA is reduced, and to mitigate the challenge of potential reverse effects.

At the time of this writing, HCA has been sold freely for approximately two and one half decades, yet the requirement for multiple doses per day for efficacy has not been overcome. The surprising finding of the instant invention is that there is a method by which the benefits of the multiple dose model can be achieved via a bolus dose without resorting to elevated levels of intake. Indeed, some benefits not otherwise reported can be achieved.

SUMMARY OF THE INVENTION

A single dosage formulation comprised of a salt form of (−)-hydroxycitric acid (HCA) in combination with glycerol is disclosed. The HCA salt form may be a potassium-magnesium salt and may be present in a single bolus dose in an amount of about 3,000 mg to 4,500 mg±20% with about 1,000 to 4,000 mg±20% of glycerol. The formulation may further comprise a flavoring agent, purified water and additional active ingredients. The formulation is preferably in a liquid form and included in a single sealed dose which can be easily opened using a screw cap or peel off top. A single dosage container of formulation is opened, and the liquid contents orally administered. The single dose is administered once a day and provides an efficacious amount of the (−)-hydroxycitric acid salt to a human patient.

The inventors have discovered that HCA surprisingly can suppress appetite and be delivered as a bolus dose, that is, once per day, without the necessity of increasing the dosage above that found to be efficacious with twice- and thrice-daily doses. One upshot of this invention is that HCA, especially in its preferred forms (potassium, sodium and potassium-magnesium hydroxycitrate), can be delivered via small vials which in the industry commonly are referred to as "shots." Other HCA salts can be utilized, such as the potassium-calcium salt and the so-called triple and quadruple salts (higher-order mixed counter-ion salts), but with enlarged volumes. The benefits include not only a reduction in the number of dosages required per day, but also reduced adverse events (limited mostly to gastrointestinal tract disturbances due to the osmolarity of concentrated salts), improved uptake, lessened interference by food (the food effect) and little chance of the appearance of reverse effects with normal diets.

It is an objective of the present invention to provide a method for delivering a daily dose of 3.0 g to 4.5 g of HCA with 1.0 g to 4 g of glycerol as a single bolus that has a therapeutic effect equal to or greater than the same amount of HCA delivered via two or three administrations (b.i.d. or t.i.d.) in the absence of glycerol.

It is a further object of the present invention to reduce the rate of occurrence of the most common adverse event with HCA salts, which is gastrointestinal intolerance.

It is a further object of the present invention to mitigate adverse effects of HCA that may occur when given to individuals on diets high in fat and/or alcohol.

It is a further object of the present invention to increase the rate of uptake of HCA while improving the overall efficiency.

An aspect of the invention includes a method of preparing a formulation wherein glycerol is mixed with water with the glycerol being present in an amount of about 1 to 3 parts by weight and the water being present in an amount of about 3 to 1 parts by weight to create a glycerol in water solution. A stable salt form of HCA is added to the 25% v/v glycerol in water solution resulting in a roughly 1.4 molar±20%, ±10%, ±5% concentration of HCA. The glycerol and water are necessarily added together prior to adding the HCA and thereafter a flavoring agent may be added as well as an additional therapeutic active agent as described here.

An aspect to the invention is a use of a single dosage formulation comprised of a salt form of (−)-hydroxycitric acid (HCA) in combination with glycerol in appetite suppression wherein the HCA is in a salt form, that may be a potassium-magnesium salt and may be present in a single bolus dose in an amount of about 3,000 mg to 4,500 mg±20% with about 1,000 to 4,000 mg±20% of glycerol for administration once a day. The use includes a formulation further comprising a flavoring agent, purified water and additional active ingredients, wherein the formulation is in a liquid form and included in a single sealed dose easily opened using a screw cap or peel off top, in a single dosage container for oral administration once a day providing an efficacious amount of the (−)-hydroxycitric acid salt to a human patient to suppress appetite.

An aspect to the invention is a method of suppressing appetite whereby HCA is orally delivered as a bolus dose, once per day, without the necessity of increasing the dosage above that found to be efficacious with twice- and thrice-daily doses, wherein the HCA, is in a salt form of (potassium, sodium and potassium-magnesium hydroxycitrate), to obtain improved uptake, lessened interference by food.

An aspect to the invention is a method for delivering a daily dose of 3.0 g to 4.5 g of HCA with 1.0 g to 4 g of glycerol as a single bolus that has a therapeutic effect equal to or greater than the same amount of HCA delivered via two or three administrations (b.i.d. or t.i.d.) in the absence of glycerol.

An aspect to the invention is a method of suppressing appetite by orally administering a single dosage formulation comprised of a salt form of (−)-hydroxycitric acid (HCA) in combination with glycerol in wherein the HCA is in a salt form, that may be a potassium-magnesium salt and may be present in a single bolus dose in an amount of about 3,000 mg to 4,500 mg±20% with about 1,000 to 4,000 mg±20% of glycerol for administration once a day, wherein the formulation further comprising a flavoring agent, purified water and additional active ingredients, wherein the formulation is in a liquid form and included in a single sealed dose easily opened using a screw cap or peel off top, in a single dosage container for oral administration once a day providing an efficacious amount of the (−)-hydroxycitric acid salt to a human patient to suppress appetite for 24 hours.

These and other objects, advantages, and features of the invention will become apparent to those persons skilled in the art upon reading the details of the method and formulation as more fully described below.

DESCRIPTION OF THE PREFERRED EMBODIMENTS

Before the present methodology and formulation are described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supersedes any disclosure of an incorporated publication to the extent there is a contradiction.

It must be noted that as used herein and in the appended claims, the singular forms "a", "an", and "the" include plural referents unless the context clearly dictates otherwise. Thus, for example, reference to "a shot" includes a plurality of such shots and reference to "the carrier" includes reference to one or more carriers and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

A method of delivery as well as a method of treatment is provided whereby a formulation or dosage is orally administered to a patient wherein each dosage unit includes an efficacious amount of (−)-hydroxycitric acid (HCA) in the form of a stable hyrdoxycitric salt as a single bolus dose in combination with glycerol. Several different stable hydroxycitric salts can be used including sodium, potassium, potassium-magnesium or magnesium hydroxycitrate; double- or triple-metal salts based on the counter ions magnesium, potassium or sodium; or any workable combination thereof.

The method may be carried out using a liquid formulation with a dosage in a single dose formulation comprised of about 3 g to 4.5 g±20%, or ±10%, or ±5%. The formulation may also be in the form of a dry powder which contains the same amount of HCA. The liquid or dry powder formulation further comprises glycerol present in an amount of 1.0 g to 4.0 g±20%, or ±10%, or ±5%.

The dosage or formulation may be further comprised of a flavoring agent and purified water. In addition, each dosage unit may be comprised of a therapeutically active agent(s), which is different from the HCA and is present in the dosage formulation in a therapeutically effective amount. The additional therapeutically active agent(s) may be selected from the group consisting of green coffee bean extract preferably ranging from 200 mg to 400 mg with an approximately 45 to 50 percent chlorogenic acid content and with the possible inclusion of caffeoylquinic and related acids; bitter melon extract preferably ranging from 750 mg to 2,000 mg; and sesame lignan extract preferably ranging from 50 to 150 mg sesamin, sesamolin or a mixture of the two.

The single dosage unit formulations may be contained within a plurality of individually sealed containers wherein each sealed container includes the appropriate dosage of HCA and glycerol with or without the additional components, flavoring agent, water, an additional therapeutically active agent. A single shot container may be grouped together with a plurality of containers. The containers may be twist off cap containers or have peel-off tops.

The free acid form, lactone and various salts of (−)-hydroxycitric acid (calcium, magnesium, potassium, sodium and mixtures thereof) are commercially available. The acid and lactone forms are no longer recommended due to the potential for chelating transition metals, such as zinc, and other minerals from the body. The lactone form is irritating to many tissues and must be converted internally to the free acid form in order to be efficacious, which takes place at a very low rate before excretion. Calcium and calcium containing HCA salts exhibit low uptake and low relative efficacy in comparison with the monovalent salts and in comparison with properly manufactured potassium-magnesium salts. The magnesium salt falls between these two groups in terms of efficacy.

The invention may be carried out with monovalent salts and the potassium-magnesium salt. Calcium salts add solubility issues that need to be overcome plus calcium interferes with the assimilation and tissue absorption of HCA and therefore calcium containing HCA salts are not recommended.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1

The following basic formula can be scaled with appropriate adjustments and used in deliveries such as single serving shots or other drink formats. The formulation comprises four ingredients: pure potassium-magnesium HCA (best at approximately 69.7% HCA), limonene, glycerol and purified water. With additional adjustments, the monovalent potassium and sodium salts and these same salts complexed with transition metals (magnesium, zinc) also can be prepared in the same manner.

| Serving Size | 1 | 1 teaspoon (5 mL) |
|---|---|---|
| Per container | 20 | 100 mL bottles |

| Material | Label Claim per serving, mg | per tsp. | net, in % | overage, in % | raw per tsp. (mg) | raw per bottle (g) | raw per batch (g) |
|---|---|---|---|---|---|---|---|
| Potassium-magnesium HCA | 1500 | 1500.00 | 69.7 | 1 | 2173.60 | 43.472 | 347.7761836 |
| Limonene | 20 | 20.00 | 100 | 1 | 20.20 | 0.404 | 3.232 |
| Glycerol (25% in Purified Water) | | make-up to 5 mL | | | ~3.5 mL | ~70 mL | |
| Active per teaspoon | | 1520.00 | | Raw per serving | 2193.80 | | |

A. Blend glycerol with purified water until dissolved completely.

B. Dissolve the potassium-magnesium hydroxycitrate into the glycerol/water component.

C. Add the limonene and stir until all items are dissolved and stable.

D. Each 5 mL supplies approximately 1,500 mg potassium-magnesium hydroxycitrate comprised of approximately 70% HCA. Preparation of drink formulas can use the material in this Example as a foundation by anyone skilled in the art of their manufacture.

Example 2

A larger and flavored version of Example 1 yielding 500 g with lemon flavor is as follows:
  344.8 g purified water
  103.44 g potassium-magnesium hydroxycitrate
  51.72 g glycerol
  0.3357 g natural flavors Example 3

For testing purposes, volunteers were given the material produced in Example 1 and asked to consume a bolus dose on one or more occasions as indicated.

Subject 1 was a middle-aged woman asked to consume 2 teaspoons at one sitting. She reported that within approximately 15 minutes she was much more wide awake with better mental acuity. This experiential mental effect is novel in terms of reports regarding HCA.

Subject 2 was a 34 year old male who consumed 2 teaspoons at one sitting. As in the case of Subject 1, he reported that within approximately 15 minutes he was much more wide awake with better mental acuity.

Subject 3 was a large middle-aged male of approximately 50 years of age who is an extreme distance runner. Consuming 2-3 teaspoons per day as a bolus dose, within the first week reported much greater endurance and better recovery.

Subject 4 was a medium build middle-aged male of approximately 50 years of age who is an distance runner. Consuming 3 teaspoons at a time bolus (4.5 grams potassium-magnesium hydroxycitrate), he reported the same rapid onset increase in mental clarity reported by Subject 1 and Subject 2. Within 1 or 2 days, he found that his endurance and recovery improved dramatically to the point that he could run a 10,000 meter course in the morning and then do weight training late in the afternoon on the same day, something he never could do before. He also reported that material produced in Example 1, he found that he suffered little or no jet lag after flying coast-to-coast, which is a regular trip for him. He further reported that in contrast to his previous experiences with taking large amounts of potassium-magnesium hydroxycitrate, even with his running schedule, he did not suffer any loose stool, an indication of better uptake of the material from the gastrointestinal tract.

Subject 4 consistently used the material produced according to the method of Example 1 for several weeks at between 4.5 g and only 3 g per day potassium-magnesium hydroxycitrate, always as a bolus, and reported no indication of any reverse effect.

Example 4

A dry powder blend of glycerol and potassium-magnesium hydroxycitrate or other acceptable HCA salts are prepared and subsequently dissolved in water. Various dry glycerol powders are available commercially and concentrated forms provide 65% glycerol by weight. The ratio of HCA-to-glycerol can be varied according to the intended usage. For athletes, the typical lower threshold of intake based upon clinical trials is 1.0 g glycerol/kg body weight, with the dosage increasing up to 3.1 g/kg body weight/day for special hydration purposes. However, a recent pilot study showed that a number of desired effects during exercise (greater tissue water retention, less loss of total body water, lower rating of perceived exertion, less decrease in plasma volume, greater "pump" meaning greater muscle volume expansion during training) can be achieved with a much lower amount of glycerol, to wit, approximately 1.56 g glycerol delivered via 2.4 g of a specialized glycerol-dried-onto-silicon dioxide powder (65% glycerol), with a recommendation of 700 mg to 2,400 mg of the powder as efficacious (455 mg to 1,560 mg glycerol). (HydroMax™ Clinical Presentation.) Hence, based upon an average 70 kg human body weight, a lower target for a blend might be 700 mg to 2,400 mg of a 65% glycerol powder matched to a daily bolus dose of 3 g to 4.5 g potassium-magnesium hydroxycitrate 70% material. The resulting powder can be mixed into an appropriate amount of water or other beverage and consumed as desired.

CONCLUSIONS (−)-Hydroxycitrate has a multitude of metabolic functions. The literature teaches that the compound requires a minimal dosage of approximately 4.5 g of a 70 percent HCA salt delivered via twice or thrice daily administration. Administration as a bolus dose to achieve similar effects typically takes four times this amount. The novel finding of the inventors is that 3 to 4.5 g can be delivered in a bolus dose in combination with glycerol to totally unexpectedly provide similar benefits without gastrointestinal distress or reverse effects.

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

We claim:
1. A sealed dosage container, comprising:
an aqueous solution of a hydroxycitrate salt and glycerol, wherein the hydroxycitrate salt is a salt of a (−)-hydroxycitric acid selected from the group consisting of sodium, potassium, potassium-magnesium, magnesium hydroxycitrate, double salts based on the counter ions magnesium, potassium and sodium, triple-metal salts based on the counter ions magnesium, potassium and sodium, and combinations thereof, present in a therapeutically effective amount sufficient to suppress appetite of a human in need thereof;
wherein the liquid sealed dosage is prepared by a process comprising:
mixing glycerol and purified water together, wherein the glycerol is present in an amount of about 1 to 3 parts by volume and the purified water is present in an amount of about 3 to 1 parts by volume to create a glycerol and purified water solution; and
dissolving the hydroxycitrate salt in the glycerol and purified water solution to obtain an hydroxycitrate salt concentration ranging from about 1.1 to 1.7 molar dosage.
2. The sealed dosage container of claim 1, wherein the hydroxycitrate salt is a stable hydroxycitrate salt.
3. The sealed dosage container of claim 1, wherein the hydroxycitrate salt is a potassium-magnesium salt of (−)-hydroxycitric acid.
4. The sealed dosage container of claim 1,
wherein the hydroxycitrate salt is a sodium salt,
wherein the glycerol is completely dissolved in the water before the hydroxycitrate salt is dissolved therein, and
wherein the aqueous solution is substantially free of lactones of the hydroxycitrate salt.
5. The sealed dosage container of claim 1, wherein the hydroxycitrate salt is present in the sealed container in amount of 3.0 g to 4.5 g±20%, and the glycerol is present in the container in an amount in a range of from 1.0 g to 4.0 g±20%.

* * * * *